(12) United States Patent
Takuma (10) Patent No.: US 7,658,191 B2
(45) Date of Patent: Feb. 9, 2010

(54) AIRWAY

(76) Inventor: Norikata Takuma, No. 793, Higashimotomachi 2 chome, Kokubunji City, Tokyo 185-0022 (JP)

( * ) Notice: Subject to any disclaimer, the term of this patent is extended or adjusted under 35 U.S.C. 154(b) by 790 days.

(21) Appl. No.: 11/317,208

(22) Filed: Dec. 23, 2005

(65) Prior Publication Data

US 2006/0213512 A1    Sep. 28, 2006

Related U.S. Application Data (63) Continuation-in-part of application No. 10/865,181, filed on Jun. 10, 2004, now Pat. No. 7,011,088.

(30) Foreign Application Priority Data

Jun. 10, 2003 (JP) .............................. 2003-164766

(51) Int. Cl.
*A61M 11/00* (2006.01)

(52) U.S. Cl. ............................ 128/207.14; 128/207.15; 128/200.26

(58) Field of Classification Search ............ 128/200.26, 128/200.24, 207.14, 207.15, 206.29, 206.16; 606/196–198, 191, 204.45
See application file for complete search history.

(56) References Cited

U.S. PATENT DOCUMENTS

| | | | |
|---|---|---|---|
| 3,774,616 A * | 11/1973 | White et al. ............ 128/200.26 |
| 3,930,507 A | 1/1976 | Berman | |
| 4,054,135 A | 10/1977 | Berman | |
| 4,198,970 A * | 4/1980 | Luomanen ............. 128/207.15 |
| 4,365,625 A | 12/1982 | Rind | |
| 4,919,126 A | 4/1990 | Baildon | |
| 5,339,805 A | 8/1994 | Parker | |
| 6,257,238 B1 * | 7/2001 | Meah .......................... 128/859 |
| 6,481,436 B1 | 11/2002 | Neame | |
| 6,517,549 B1 * | 2/2003 | Dennis ....................... 606/108 |
| 6,679,901 B1 | 1/2004 | Takuma | |
| 6,983,744 B2 * | 1/2006 | Alfery .................... 128/200.26 |
| 2001/0013344 A1 | 8/2001 | Chou | |
| 2003/0131853 A1 | 7/2003 | Wall et al. | |
| 2003/0192549 A1 | 10/2003 | Boussignac | |
| 2004/0129272 A1 | 7/2004 | Ganesh et al. | |

* cited by examiner

*Primary Examiner*—Steven O Douglas
(74) *Attorney, Agent, or Firm*—Dilwortth & Barrese LLP (57) ABSTRACT

A medical instrument which improves a state of falling of a tongue root of a patient to makes it easy to maintain an air passage in a pharynx portion. An airway of the present invention includes an airway main body wherein an elongated tongue plate curved in a longitudinal direction to match a curved surface shape of a tongue, and an elongated palate plate curved approximately similarly to the elongated tongue plate, are connected by two side plates and an inward member which includes a groove portion provided on the surface of the inward member to define a hole for air to pass air therethrough when the inward member fits into the airway main body.

13 Claims, 11 Drawing Sheets fig1 fig2 fig3 fig4 fig5

AIRWAY

CROSS REFERENCE TO RELATED APPLICATIONS

The present application is a continuation-in-part of U.S. application Ser. No. 10/865,181 filed Jun. 10, 2004 now U.S. Pat. No. 7,011,088, the contents of which are incorporated by reference herein.

BACKGROUND OF THE INVENTION

1. Field of the Invention

The present invention relates to medical equipment for helping a patient to breathe in a medical field, more specifically, to an improvement of a medical instrument, referred to as a so-called "airway", which improves a state of falling of a tongue root of a patient to maintain an air passage in a pharynx portion.

2. Description of the Related Art

Figure 7:
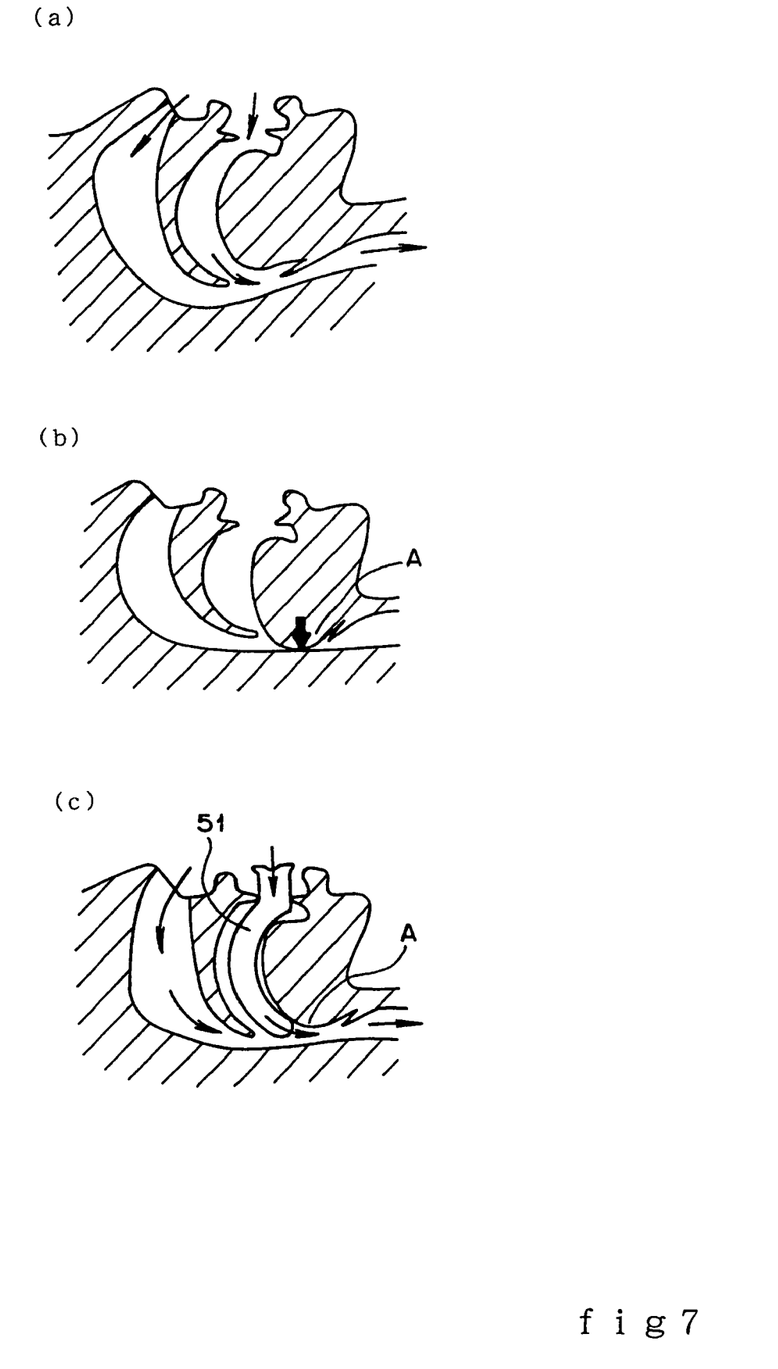
Figure 8:
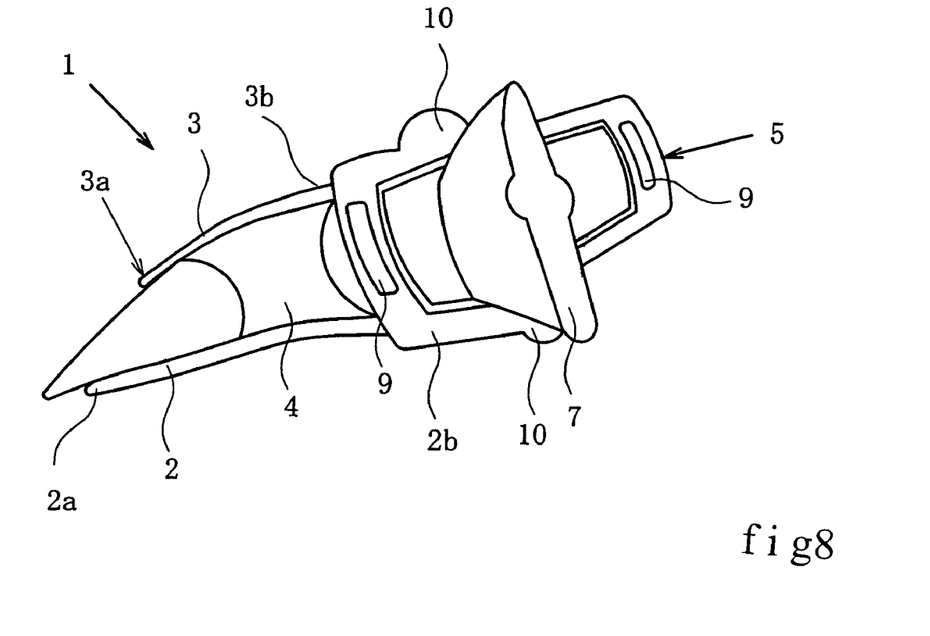
FIG. 8 is a perspective view similar to FIG. 1 and showing another embodiment of an airway according to the present invention which is used.
Figure 9:
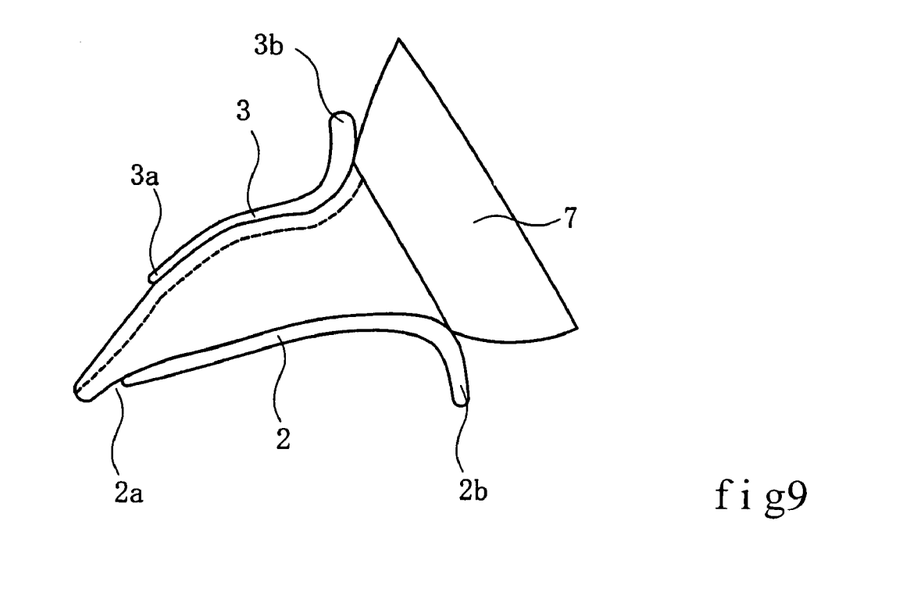
FIG. 9 is a cross sectional view of FIG. 8.
Figure 10:
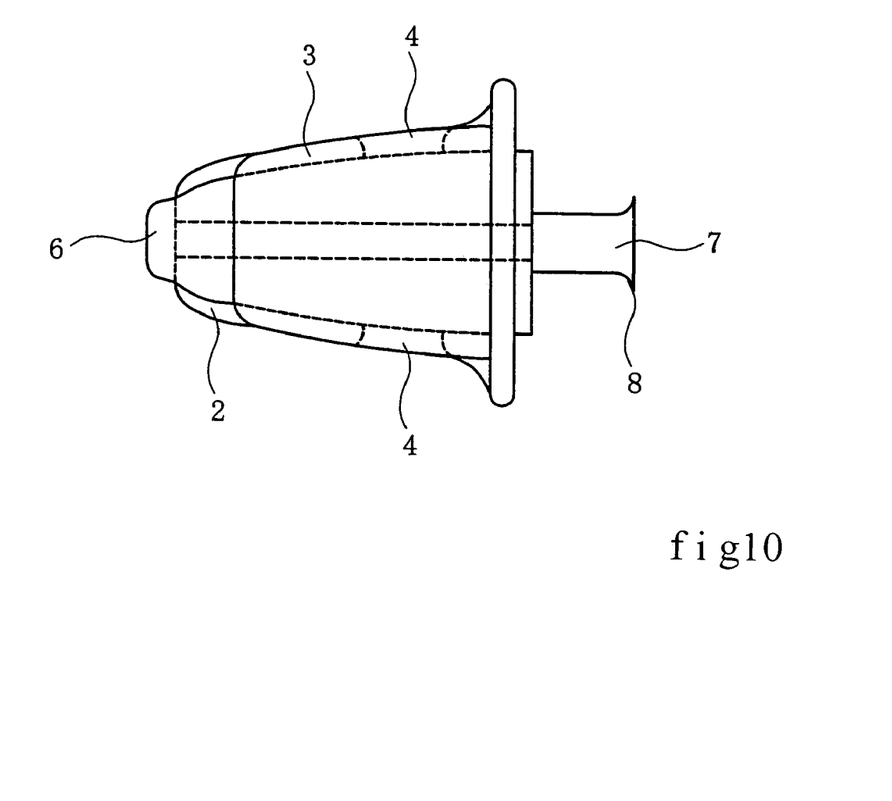
FIG. 10 is a plan view of FIG. 8.
Figure 11:
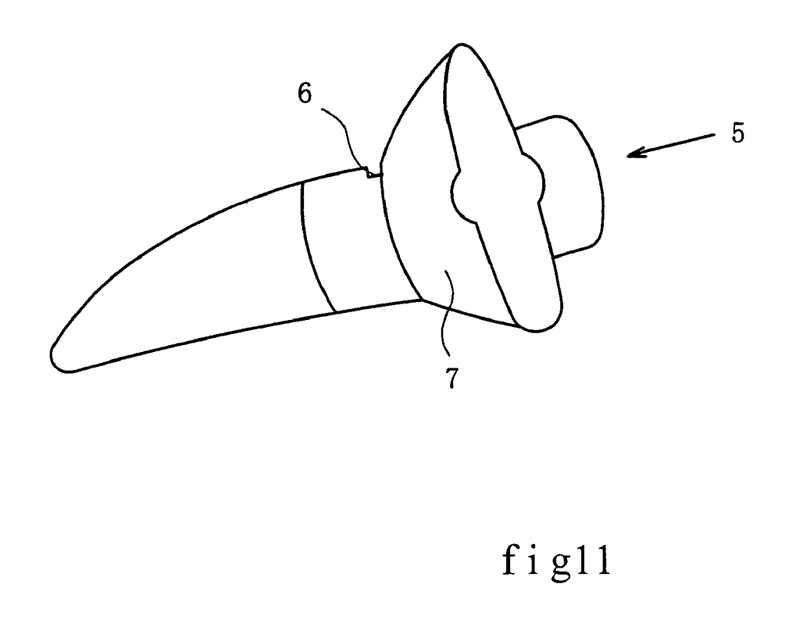
FIG. 11 is a perspective view showing an inward member of FIG. 8.
Figure 12:
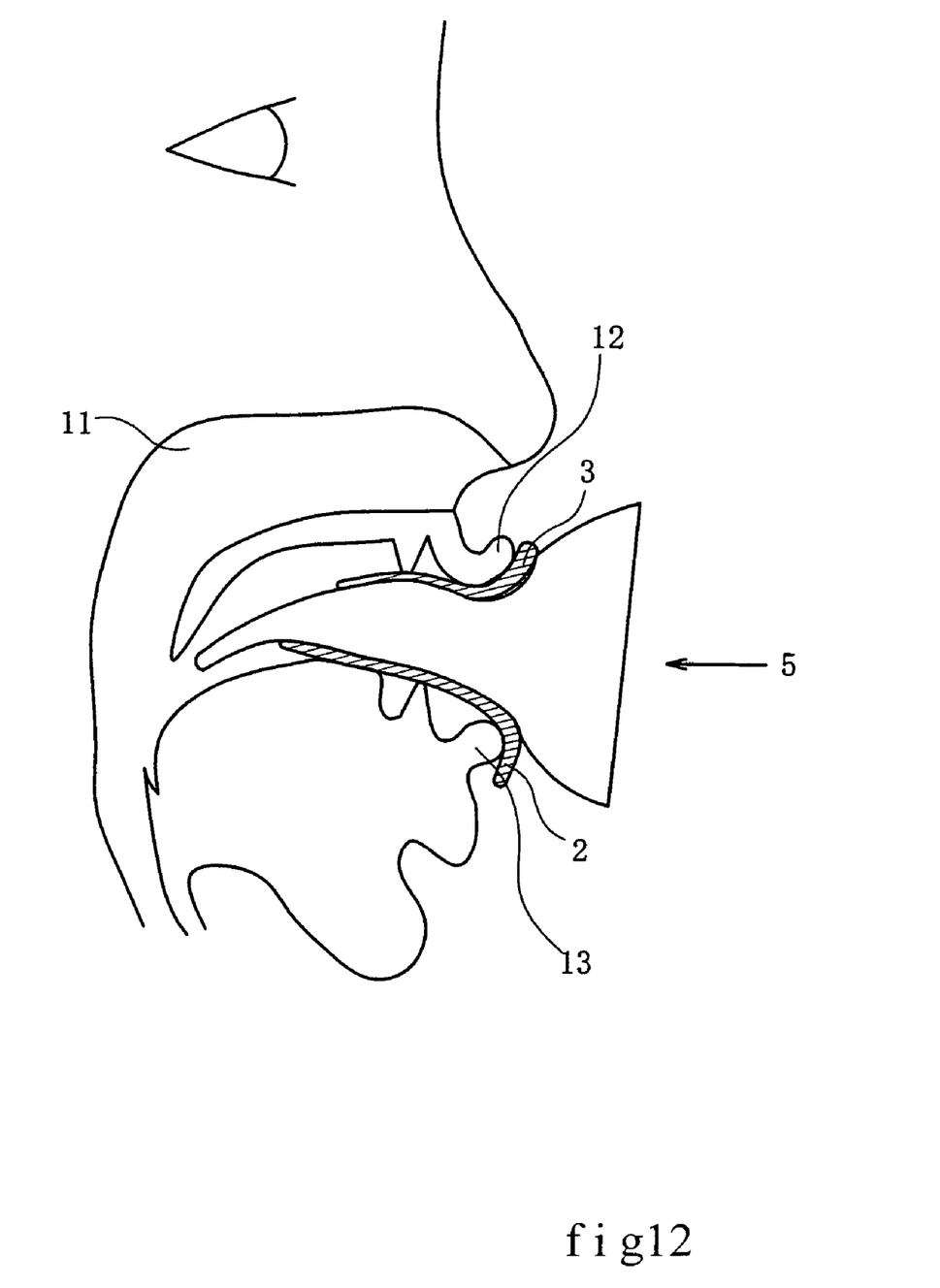
FIG. 12 is a schematic cross sectional side view similar to FIG. 5 and showing a condition in which the airway of FIGS. 8-11 is inserted into a pharynx portion.
Figure 13:
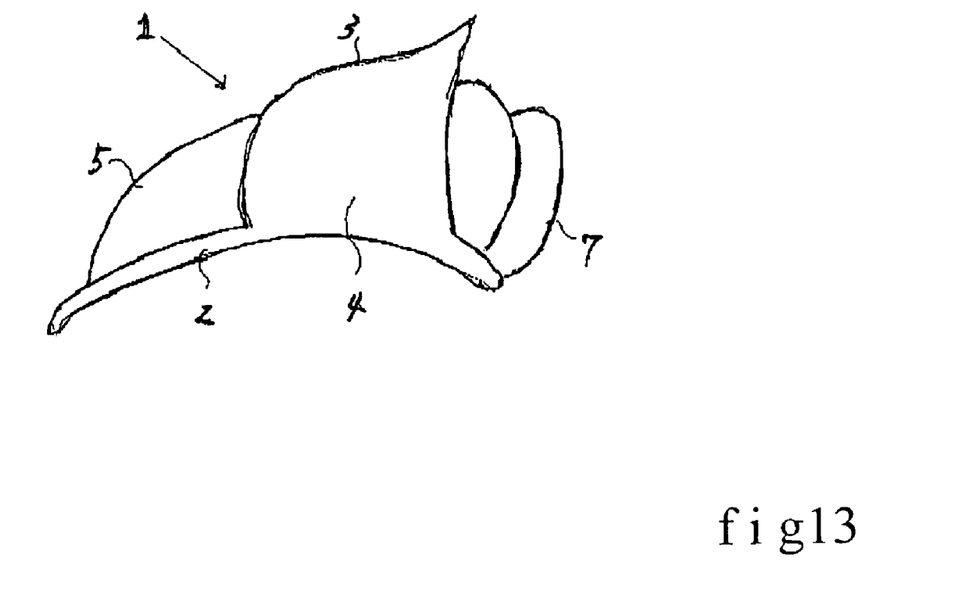
FIG. 13 is a side view illustrating a further embodiment of an airway of the present invention.
Figure 14:
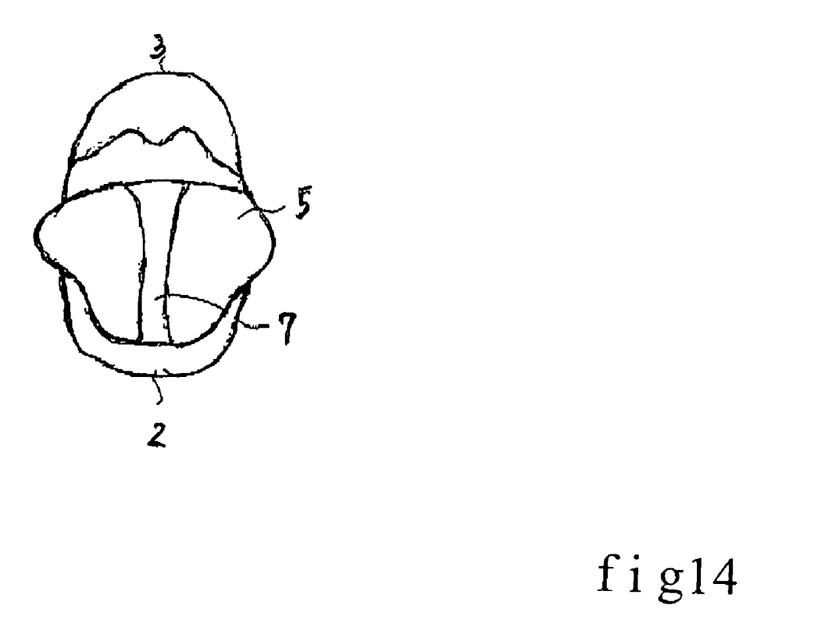
FIG. 14 is a right side view of FIG. 13.
Figure 15:
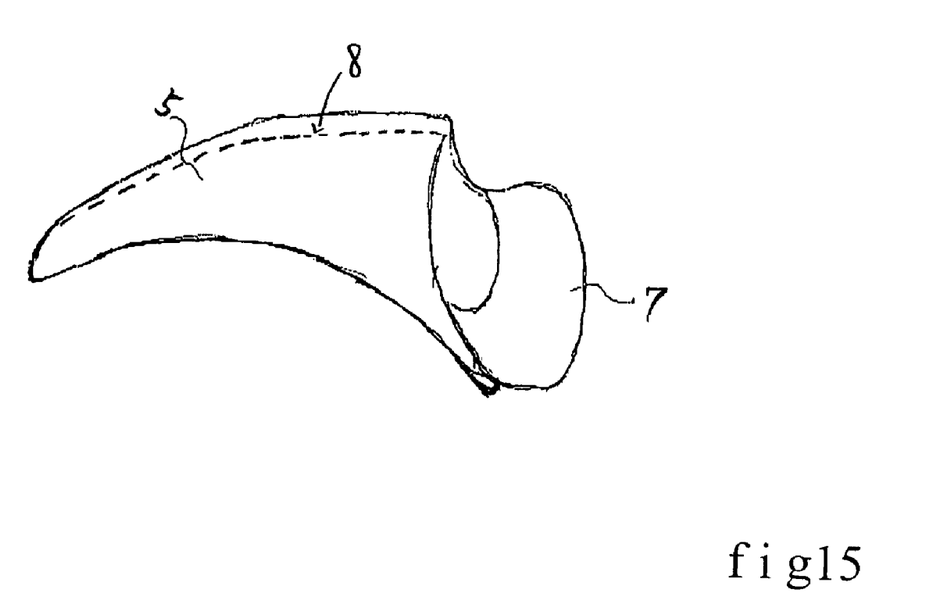
FIG. 15 is a perspective view showing the inward member of FIGS. 13 and 14.
Figure 16:
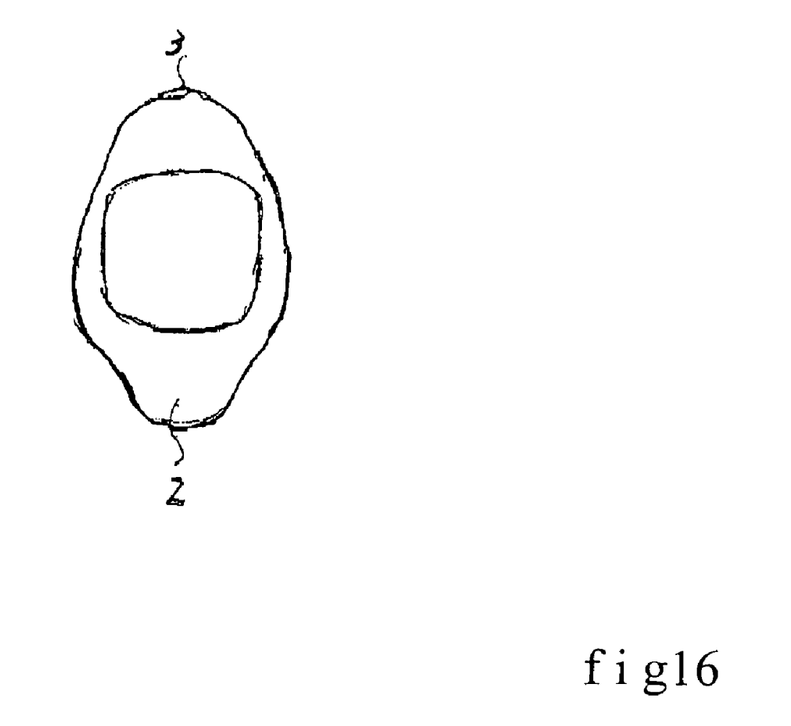
FIG. 16 is a right side view of the airway of FIGS. 13 and 14 and with the inward member removed.

In a normal case, one can breathe easily even when one is lying on one's back because an air passage in a pharynx portion is maintained to allow an air to pass behind a tongue root (see FIG. 7(a)). In a case of a consciousness disorder, however, one will fall into a state of difficulty in breathing when one is lying on one's back because the tension of a muscle is lost so that a tongue root may fall into and block a passage, through which air passes, that is, an air passage in a pharynx portion (see FIG. 7(b)). This necessarily allows the condition of the patient to take a turn for the worse.

Figure 6:
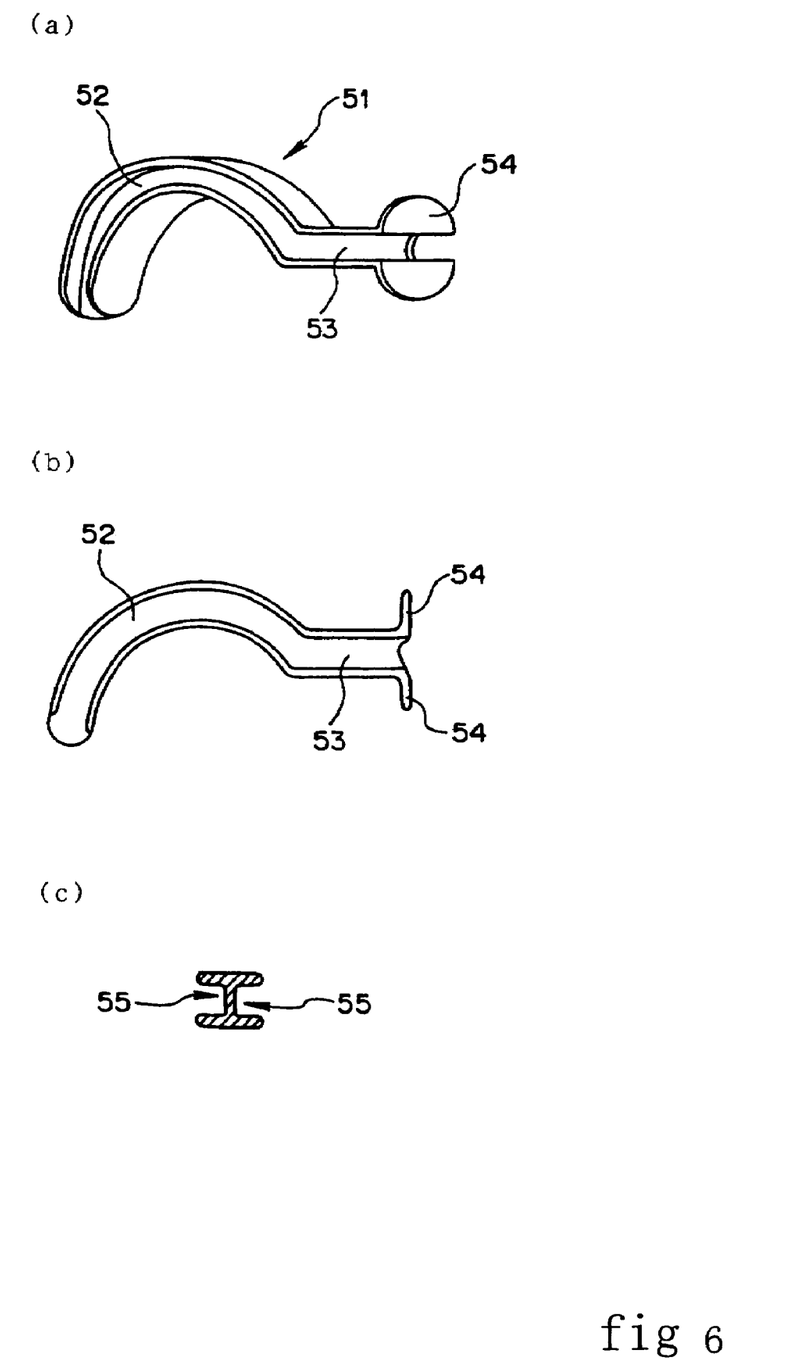

In such a case, it is required in one way or another to provide a passage necessary for breathing (to maintain an air passage) to allow a patient to be able to breathe easily. In this case, a medical instrument 51, referred to as a so-called "airway", as shown in FIG. 6, is generally used, the medical instrument 51 comprising an umbrella-shaped stopping portion 54 for handling which will be exposed to the outside of a mouth, a linear introducing portion 53 which transits from the umbrella-shaped stopping portion 54 to a portion for an oral cavity, and a curve-shaped oral cavity inserting portion 52 which is continued to the linear introducing portion 53, the medical instrument 51 being of approximately H-shaped cross section, and having concave recessing portions 55 and 55, which define spaces for breathing on both sides of the instrument 51, wherein the medical instrument 51 can be inserted from a mouth into a pharynx portion to elevate a tongue root portion A to maintain an air passage in the pharynx portion (see FIG. 7(c)).

However, the above-mentioned medical instrument does not always match the shape of a tongue, which sometimes may lead to a constrained state. Although a tongue which comprises a mass of sarcous can be deformed according to conditions, its entire profile can have a natural curve without strained convex or concave. However, following a portion transiting from the portion for an outside of a mouth to the portion for an oral cavity, the above-described medical instrument bends at a steep angle not only at the portion transiting from the linear introducing portion to the curve-shaped oral cavity inserting portion, but also is curved at a steep angle at the curve-shaped oral cavity inserting portion. As a result, the bending portion and the curved portion of the medical instrument tend to press a tongue in a direction to a tongue root.

In addition, the above-mentioned medical instrument is difficult to insert into a pharynx portion. That is, the instrument has the demerit of being very hard to manipulate because the instrument has a specifically fixed shape as noted above, so that the bending portion and/or the curved portion thereof may often hit against a portion, such as a lip, an incisor, or a palate and so on during the insertion.

Further, it is difficult to aspirate phlegm when using the above-mentioned medical instrument. That is, since a tube for aspiration is inserted through either one of the concave recessing portions on both sides of the instrument with approximately H-shaped cross section and the instrument has a specifically fixed shape as stated above, the tube for aspiration may be caught on the bending portion and/or the curving portion and cannot go into further.

Furthermore, a tongue root is not sufficiently elevated when using the above-mentioned medical instrument. Since the object of the instrument of this type is to maintain an air passage in a pharynx portion by inserting the instrument of the above-described specific fixed shape between a tongue and a palate, a space for an air passage obtained is limited by the size of the cross section of the instrument. If the cross sectional area of the instrument is provided to be large enough to elevate a tongue sufficiently, another inconvenience occurs instead, that is, it becomes more difficult to insert the instrument due to its specific shape.

Additionally, the above-mentioned medical instrument after using is not easy to clean. Considering problems of hygiene and disinfection of medical instruments from the viewpoint of bacterial proliferation, when proteins remain on the surface of an instrument, an effect of a disinfectant will decrease greatly thereby allowing bacteria to proliferate easily. The above-stated instrument has many concave recessing portions which are not easy to clean due to the approximately H-shaped of the cross section as stated above.

SUMMARY OF THE INVENTION

Therefore, in order to solve such problems, the inventor of the present invention researched thoroughly and found that the problem can be addressed by using: an airway main body 1 wherein two elongated plate members gently curved in a longitudinal direction to be inserted into a pharynx portion easily as well as to match a curved surface shape of a tongue are connected to each other with side plates; and an inward member 5 with a lug portion, which includes an air vent and is adapted to fit into the airway main body.

A first embodiment of the present invention is an airway comprising: an airway main body 1 comprising an elongated tongue plate 2 curved in a longitudinal direction and an elongated palate plate 3 connected by side plates 4 provided on a side of the elongated tongue plate 2; and an inward member 5 which includes a hole for air 6 and is adapted to fit into the airway main body 1.

A second embodiment of the present invention is an airway, wherein the elongated tongue plate 2 curved in a longitudinal direction has a length longer than the elongated palate plate 3, and when the inward member 5 fits into the airway main body 1, front end portions form a smooth curved surface as a whole. This shape makes it easy to insert the instrument into a mouth of a patient.

A third embodiment of the present invention is an airway, wherein the airway main body 1 has an axial cross-section of approximately tetragonal shape gradually narrower from an insertion portion toward a distal end portion and wherein the inward member 5 is in such a shape as to fit into and along an inner surface of the airway main body 1.

A fourth embodiment of the present invention is an airway, wherein an evaginated portion for preventing both rear end portions of the elongated tongue plate 2 and the elongated palate plate 3 from being inserted into a mouth are provided on both the rear end portions of the elongated tongue plate 2 and the elongated palate plate 3 of the airway main body 1.

A fifth embodiment of the present invention is an airway, wherein the evaginated portion is provided with a projecting portion 10 on which a tape or the like is stuck for fixation, and holes for strings 9 provided on both end portions.

A sixth embodiment of the present invention is an airway, wherein the inward member 5 includes at least one or more holes for air 6 in a portion 5 for an oral cavity.

A seventh embodiment of the present invention is an airway wherein the inward member 5 has a lug portion 7 comprising a small projection or a hole on a portion for an outside of a mouth.

In an eight embodiment of the present invention, a groove portion is provided on the surface of the inward member 5 from an upper portion to a bottom portion side of a lug portion 7 to define a passage for air 6 therethrough when the inward member 5 fits into the airway main body 1. The inward member 5 omits the hole 6 through the interior thereof. The rear edge of the lug portion 7 is flat.

In a ninth embodiment of the present invention, the elongated tongue plate 2 of the airway curved in a longitudinal direction has a length substantially longer than the palate plate 3, and when the inward member 5 fits into the airway main body 1, a front end portion of the inward member 5 forms a smooth curved surface as an exposed upper surface facing the palate and containing a groove to facilitate breathing. This shape makes it easy to insert the instrument into a mouth of a patient. The front end of the inward member has a laterally expanded lug portion to retain the inward member against the airway main body 1. The inward member 5 may include a plurality of holes or grooves 8 for air on a top portion thereof when inserted into the airway main body 1.

BRIEF DESCRIPTION OF THE DRAWINGS

FIG. 6(*a*) is a perspective view showing a conventional airway;

FIG. 6(*b*) is a side view showing a conventional airway;

FIG. 6(*c*) is a schematic longitudinal cross sectional side view showing a conventional airway;

FIG. 7(*a*) is a schematic cross sectional side view showing a condition of an air passage when one is lying on one's back;

FIG. 7(*b*) is a schematic cross sectional side view showing a condition of a blocked air passage when one is lying on one's back;

FIG. 7(*c*) is a schematic cross sectional side view showing a condition in which a conventional airway is inserted into a pharynx portion;

DESCRIPTION OF THE PREFERRED EMBODIMENTS

Figure 1:
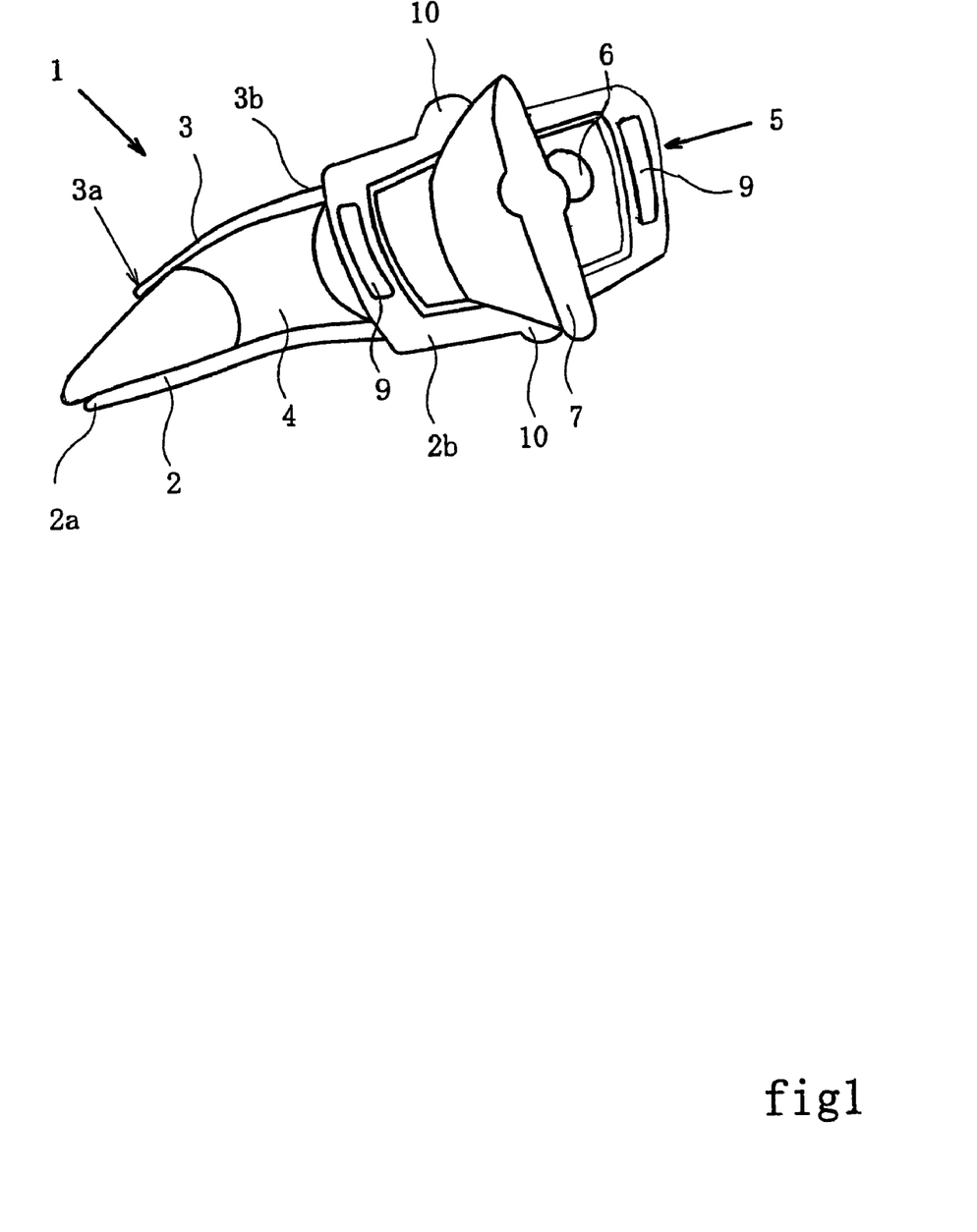
FIG. 1 is a perspective view showing an embodiment of an airway according to the present invention which is used.
Figure 2:
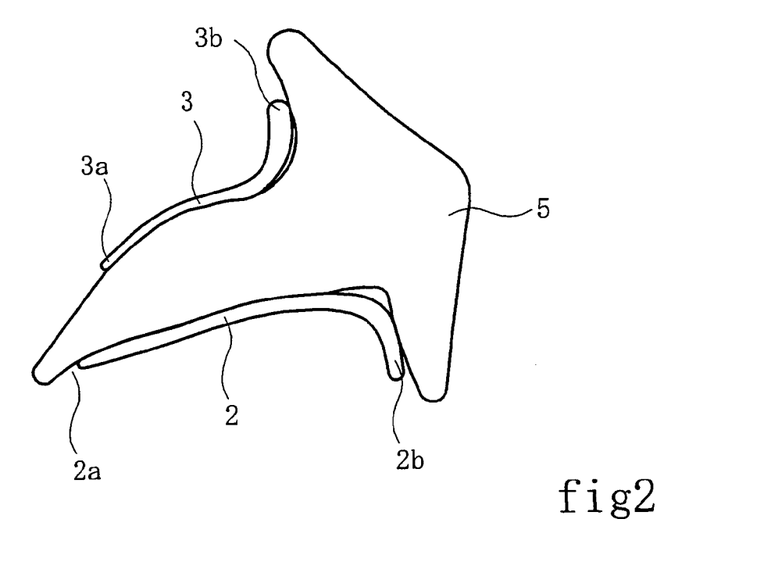
FIG. 2 is a cross sectional view of FIG. 1.
Figure 3:
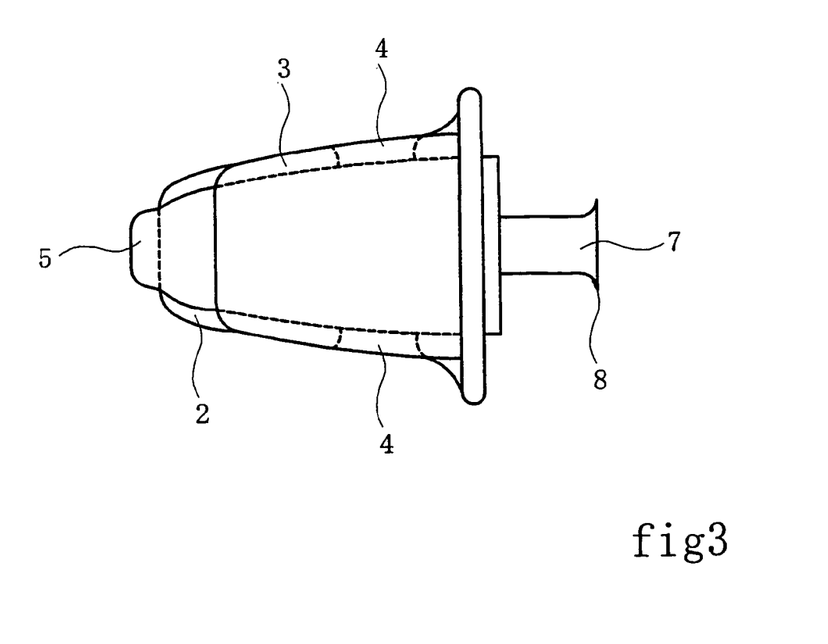
FIG. 3 is a plan view of FIG. 1.
Figure 4:
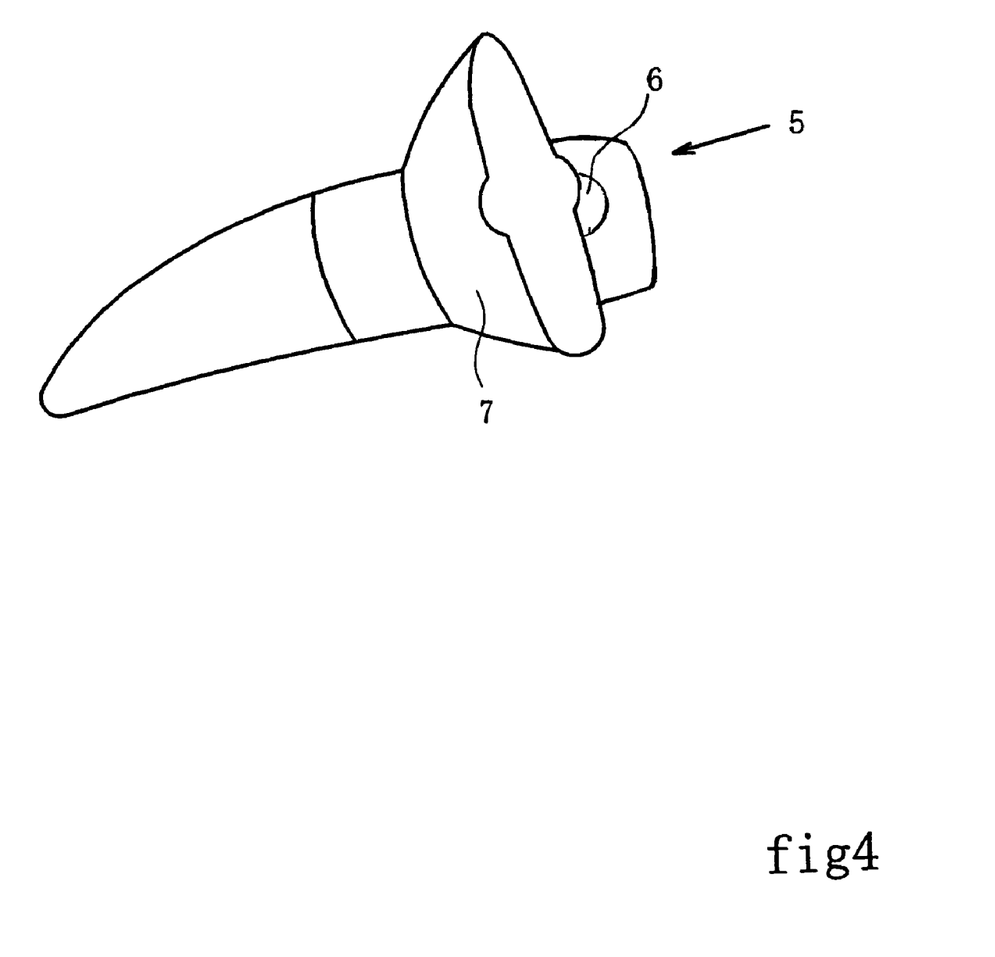
FIG. 4 is a perspective view showing an inward member of FIG. 1.

An airway 1 according to the present invention is made of hard plastic or synthetic resin as a whole. As shown in FIGS. 1 to 3, the airway of the present invention has a construction wherein an elongated tongue plate 2 curved in a longitudinal direction to match a curved surface shape of a tongue, and an elongated palate plate 3 curved approximately similar to the elongated tongue plate 2, are connected to each other by two side plates 4. With this structure, when elevating a tongue root by a front end of the tongue plate and extracting a central member 5, a space through a central portion can be made. As a result, passing of air for breathing, which is an essential object of the airway, can be performed easily, and at the same time, aspiration and medical treatments can be performed easily. These are improvements compared with the conventional airways.

Figure 5:
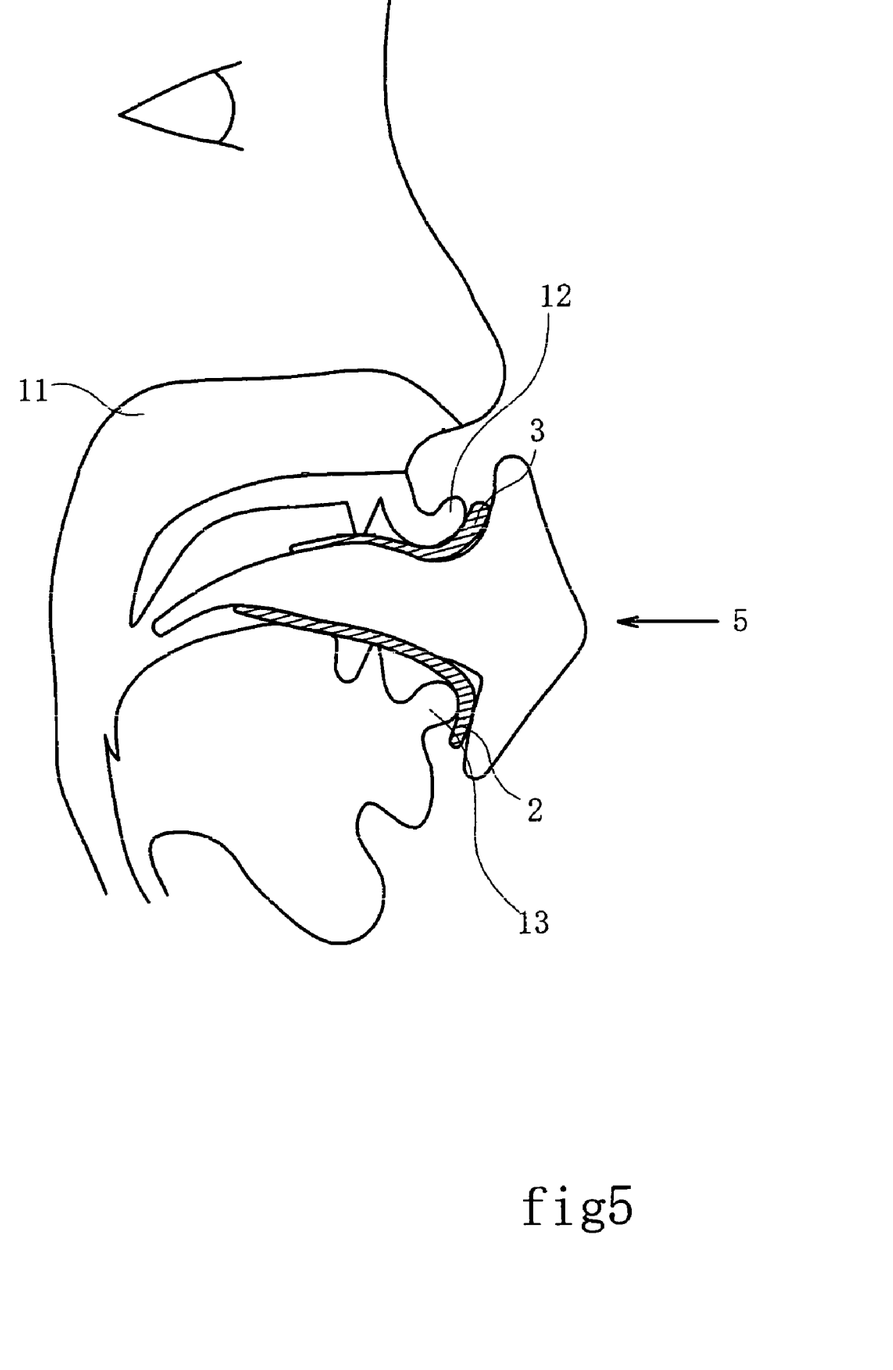
FIG. 5 is a schematic cross sectional side view showing a condition in which an airway of the present invention is inserted into a pharynx portion.

In this case, the inward member 5 which can fit into the airway main body 1 has such a shape as to closely fit to a hollow portion of the airway main body 1 when using. As shown in FIG. 5, the instrument is inserted into a mouth of a patient in a condition in which the inward member 5 is kept fitting in the airway main body 1. Moreover, the reference numeral 11 indicates a nasal cavity.

Both of the airway main body 1 and the inward member 5 of the present invention represent divergence with a gentle curve from front end portions to entrance portions. As a result, the structure of the airway main body 1 and the inward member 5 is easy to insert from a mouth of a patient gradually toward a deep portion of an oral cavity. As shown in FIGS. 1 and 2, the elongated tongue plate 2 includes a front end portion 2*a*, and the elongated palate plate 3 includes a front end portion 3*a*.

In addition, both rear ends of the airway main body 1 and the inward member 5 have a construction wherein the ends are evaginated. This structure can make the airway inserted properly, because only the airway main body 1 remains in an oral cavity, if the inward member 5 which is kept fitting in the airway main body 1 is extracted with its pull at the time when the rear ends of both the airway main body 1 and the inward member 5 are caught on lips of a patient during insertion.

In such a case, it is preferable that the airway main body 1 be fixed with tapes or the like (not shown) stuck over projecting portions 10 provided on the evaginated portion in order to hold the airway stable when the rear ends are caught on lips of a patient. Moreover, holes for strings 9 are provided on both sides of the evaginated portion so that the airway may be easy to store.

In addition, the inward member 5 has at least one or more air vents or holes for air 6 provided in an inward portion 5 or a portion for an oral cavity as well as a lug 7 comprising a small projection 8 or a hole on a portion for an outside of a mouth. Therefore, even if the airway of the present invention is inserted into a mouth of a patient in a condition in which the inward member 5 is kept fitting into the airway main body 1, this structure ensures that air can pass into a body of a patient through the above-stated air vents.

In this case, it is preferable that the members of the airway main body 1, the inward member 5 or the like be formed not in an angulated shape but in a rounded shape so that the members may not injure an oral cavity as well as the members may be easy to clean.

The airway constructed as stated above, as shown in FIG. 5, is inserted into a deep portion of an oral cavity by inserting the airway from a mouth into a pharynx portion in a condition in which the airway main body 1 and the inward portion 5 are kept fitting to each other, and then, a rear end portion 2*b* of the elongated tongue plate 2 and a rear end portion 3*b* of the elongated palate plate 3 are caught on upper and lower lips 12, 13 to prevent the airway from further invading the interior.

Next, when the inward portion 5 is pulled out with the lug portion 7 toward the outside, a space for breathing can be ensured between the elongated tongue plate 2, the elongated palate plate 3 and both of the side plates 4, as well as the front end portion of the elongated tongue plate 2 elevates a tongue root A so that an air passage can be maintained to avoid respiratory disorder due to falling or dropping of a tongue root. As a result, insertion of medical instruments such as an elevation member of the tongue root portion A, a tube for aspiration, or the like can be easily performed.

In addition, the present invention is also an airway which functions as a through passage in a longitudinal direction for insertion of medical instruments wherein the insertion of medical instruments such as a tube for aspiration, optical fibers, or the like can be performed still more easily because the interior of the airway main body 1 is a hollow shape or hollow.

Moreover, the present invention is also an airway wherein a more preferable environment for observation of a pharynx portion can be created by irradiating the pharynx portion brightly with light from a light source outside a mouth through front end portions of optical fibers which is realized by embedding optical fibers in a hollow body along and in a longitudinal direction similarly as stated above, and by connecting the optical fibers with a connecting member to other optical fibers provided outside the mouth.

Furthermore, the present invention is also an airway wherein a more preferable environment for observation of a pharynx portion can be created by making an elongated tongue plate from a transparent member so that light from a light source outside a mouth can be transmitted or refracted within the elongated tongue plate, resulting in the pharynx portion similarly illuminated brightly.

As stated above, according to the present invention, since an approximately tetragonal or rectangular space is made by two side plates and two elongated plate members comprising an elongated tongue plate and an elongated palate plate, it becomes possible to ensure between the plates and the members a passage for insertion of medical instruments such as a tube for aspiration or the like, or a space for breathing which passes in the longitudinal direction.

In addition, since a large space for breathing or a passage for insertion of medical instruments is maintained at a center portion in the longitudinal direction, it becomes easier to perform aspirating manipulation of phlegm or the like and inserting manipulation of other medical instruments such as a tube for aspiration can become easier. And at the same time, it also becomes possible to make a direct visual check of a pharynx portion, which was impossible with conventional types of medical instruments (airways).

Moreover, according to the present invention, rear end portions of an elongated tongue plate and/or an elongated palate plate are provided in such a manner as to be widely curved in the separated and opposite direction to each other, it is possible to make a direct visual observation of a pharynx portion within the range of their angle. Besides, a potential hazardous condition in which the airway itself sometimes excessively falls into an oral cavity can be avoided because the rear ends are curved in such a manner as to broaden or expand.

Further, according to the present invention, a through passage in a longitudinal direction for insertion of medical instruments is provided inside or on a surface of an elongated tongue plate so that medical instruments such as a tube for aspiration of phlegm or the like can bend according to the shape of the elongated tongue plate to go easily into the depth without deviating from a proper position. As a result, it becomes possible to insert the medical instruments still more easily.

Furthermore, according to the present invention, it becomes possible to create more preferable environment for observation of a pharynx portion by illuminating the pharynx portion brightly with light from a light source outside a mouth, which is realized by embedding optical fibers within an elongated tongue plate along in a longitudinal direction or by making the elongated tongue plate of a transparent member.

In addition, according to the present invention, since an airway main body 1 and an inward member 5 are detachably connected with each other, it is possible to clean them fully sanitarily by brushing them in any directions if they are detached each other.

In the embodiment of FIGS. 8-16, similar components have been denoted by the same reference numerals as in the embodiment of FIGS. 1-7. FIGS. 8-12 show another embodiment of an airway according to the present invention which is used. In this embodiment, there is provided an airway, wherein the inward member 5 omit the hole 6 in the interior portion 5 thereof. Instead, the inward member 5 includes a groove portion 6 along a central top portion of the inward member 5 for an oral cavity, to facilitate breathing during insertion. The shape of the rear end of the lug portion 7 is flat.

FIGS. 13-16 show a further embodiment of an airway according to the present invention which is used. In this embodiment, there is provided an airway, wherein the elongated tongue plate 2 curved in a longitudinal direction has a length substantially longer than the palate plate 3, and when the inward member 5 fits into the airway main body 1, a front end top portion of the inward member 5 form a smooth, exposed curved surface as a whole. This shape makes it easy to insert the instrument into a mouth of a patient. The inward member 5 may include a plurality of holes or grooves 8 for air on a top portion thereof. Additionally, the rear end of the inward member 5 has laterally expanded portion (FIG. 14) to retain the inward member 5 in the airway main body 1 when inserted thereinto.

The preceding description of the present invention is merely exemplary and not intended to limit the scope thereof.

What is claimed is:

1. An airway comprising:
   an airway main body comprising an elongated tongue plate curved in a longitudinal direction and an elongated palate plate connected by side plates provided on a side of the elongated tongue plate; and
   an inward member which is adapted to fit into the airway main body,
   wherein a groove portion is provided on a surface of the inward member from an upper portion to a bottom portion side of a lug portion on the inward portion so that a hole for air can be defined to pass air therethrough when the inward member fits into the airway main body.

2. An airway according to claim 1, wherein the elongated tongue plate curved in a longitudinal direction has a length longer than the elongated palate, and when the inward member fits into the airway main body, front end portions form a smooth curved surface.

3. An airway according to claim 1, wherein the airway main body has an axial cross-section of approximately tetragonal shape gradually narrower from an insertion portion toward a front end portion and wherein the inward member is in such a shape as to fit into and along an inner surface of the airway main body.

4. An airway according to claim 1, wherein an evaginated portion for preventing both rear end portions of the elongated tongue plate and the elongated palate plate from being inserted into a mouth are provided on both the rear end portions of the elongated tongue plate and the elongated palate plate of the airway main body.

5. An airway according to claim 4, wherein the evaginated portion is provided with a projecting portion on which a tape or the like is stuck for fixation, and holes for strings provided on both end portions.

6. An airway according to claim 1, wherein the inward member has a lug portion comprising a small projection or a hole on a portion for an outside of a mouth.

7. An airway according to claim 1, wherein said groove is defined a top surface of the inward member when inserted into the airway main body.

8. An airway according to claim 1, wherein a shape of a rear end of the inward member is substantially flat.

9. An airway according to claim 7, wherein a plurality of grooves for air are provided on top surface of the inward member when inserted into the airway main body so that a hole for air can be defined to pass air therethrough when the inward member fits into the airway main body.

10. An airway according to claim 9, wherein the elongated tongue plate curved in a longitudinal direction has a length substantially longer than the palate, and when the inward member fits into the airway main body, front end portions form a smooth curved surface.

11. An airway comprising:
an airway main body having an elongated tongue plate curved in a longitudinal direction, and extending out from a circular hollow portion; and
an inward member structured and arranged to be inserted into and retained in said airway main body and define an upper exposed surface opposite said tongue plate when inserted thereinto,
wherein said inward member has a laterally expanded portion retaining said member in said hollow portion when inserted into said airway main body.

12. An airway comprising:
an airway main body having an elongated tongue plate curved in a longitudinal direction, and extending out from a circular hollow portion; and an inward member structured and arranged to be inserted into and retained in said airway main body and define an upper exposed surface opposite said tongue plate when inserted thereinto,
wherein said inward member comprises at least one groove along a top surface thereof when inserted in said airway main body to facilitate breathing.

13. An airway according to claim 11, wherein said inward member comprise at least one groove along a top surface thereof when inserted in said airway main body to facilitate breathing.

* * * * *